(12) United States Patent
Zou et al.

(10) Patent No.: US 10,689,309 B1
(45) Date of Patent: Jun. 23, 2020

(54) FUSED-RING ALKANE FUEL AND PHOTOCATALYTIC PREPARATION PROCESS THEREOF

(71) Applicant: TIANJIN UNIVERSITY, Tianjin (CN)

(72) Inventors: Jijun Zou, Tianjin (CN); Lun Pan, Tianjin (CN); Xiangwen Zhang, Tianjin (CN); Qingfa Wang, Tianjin (CN)

(73) Assignee: TIANJIN UNIVERSITY, Tianjin (CN)

( * ) Notice: Subject to any disclaimer, the term of this patent is extended or adjusted under 35 U.S.C. 154(b) by 0 days.

(21) Appl. No.: 16/498,386

(22) PCT Filed: Jul. 9, 2018

(86) PCT No.: PCT/CN2018/095036
§ 371 (c)(1),
(2) Date: Sep. 27, 2019

(87) PCT Pub. No.: WO2020/010494
PCT Pub. Date: Jan. 16, 2020

(30) Foreign Application Priority Data

Jul. 9, 2018 (CN) .......................... 2018 1 0744542

(51) Int. Cl.
*C10L 1/04* (2006.01)
*C07C 1/247* (2006.01)

(52) U.S. Cl.
CPC ............... *C07C 1/247* (2013.01); *C10L 1/04* (2013.01); *C07C 2521/04* (2013.01); *C07C 2521/06* (2013.01); *C07C 2521/08* (2013.01); *C07C 2523/06* (2013.01); *C07C 2523/10* (2013.01); *C07C 2523/30* (2013.01); *C07C 2529/40* (2013.01); *C07C 2529/70* (2013.01); *C07C 2602/24* (2017.05)

(58) Field of Classification Search
CPC ... C07C 201/08; C07C 205/02; C07C 205/05; C07C 205/15; C07C 59/72; C10L 1/02; C10L 1/04
See application file for complete search history.

(56) References Cited

FOREIGN PATENT DOCUMENTS

CN 101456858 A 6/2009
CN 108191599 A 6/2018

OTHER PUBLICATIONS

Fang Chen et al. Synthesis of High-Density Aviation Fuel with Cyclopentanol, ACS Sustainable Chemistry & Engineering, Oct. 2, 2016, vol. 4, pp. 6160-6166.

Genkuo Nie, et al. One-pot production of branched decalins as high-density jet fuel from monocyclic alkanes and alcohols, Chemical Engineering Science, 180(2018), pp. 64-69.

Junjian Xie et al. Synthesis of High-Density Liquid Fuel via Diels-Alder Reaction of Dicyclopentadiene and Lignocellulose-Derived 2-Methyfuran, Catalysis Today, vol. 319, Apr. 25, 2018, pp. 139-144.

*Primary Examiner* — Sharon Pregler
(74) *Attorney, Agent, or Firm* — Bayramoglu Law Offices LLC

(57) ABSTRACT

A process for preparing a fused-ring alkane fuel, wherein the fused-ring alkane fuel has the following structure:

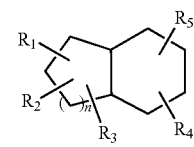

wherein n is 1 or 2; $R_1$, $R_2$, $R_3$, $R_4$ and $R_5$ are H or —$CH_3$ or —$CH_2CH_3$;
the fused-ring alkane fuel has a density of greater than 0.870 g/cm³, a freezing point of not higher than −50° C., and a net mass heat value of not less than 42.0 MJ/kg; the process for preparing a fused-ring alkane fuel, wherein the process includes steps of: (1) in a presence of ultraviolet light and a photocatalyst, a Diels-Alder cycloaddition reaction between a substituted or unsubstituted cyclic enone and a substituted or unsubstituted furan molecule occurs to produce a fuel precursor molecule:

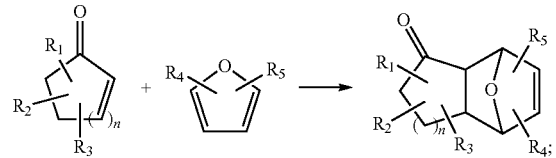

(2) the fuel precursor molecule obtained in the step (1) is subjected to hydrodeoxygenation to produce the fused-ring alkane fuel.

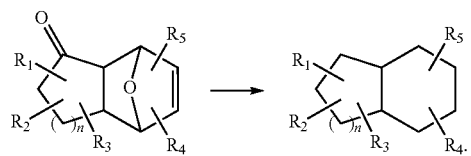

9 Claims, No Drawings

FUSED-RING ALKANE FUEL AND PHOTOCATALYTIC PREPARATION PROCESS THEREOF

CROSS REFERENCE TO THE RELATED APPLICATIONS

This application is the national phase entry of International Application No. PCT/CN2018/095036, filed on Jul. 09, 2018, which is based upon and claims priority to Chinese Patent Application No. 2018107445428, filed on Jul. 9, 2018, the entire contents of which are incorporated herein by reference.

TECHNICAL FIELD

The invention is in the technical field of liquid fuel propellant, and particularly, it relates to a high density liquid fuels of fused-ring alkane and a preparation process thereof via a photocatalytic Diels-Alder cycloaddition reaction.

BACKGROUND

High density hydrocarbon fuel is an important component of liquid propellants for aircrafts, being a key for providing power guarantee for aircrafts such as airplanes, missiles and rockets, and thus, the quality of the fuel will decide the flight performances (including flying range, flying speed, and effective loads) of the aircrafts. For an aerospace aircraft having a definitive volume, the higher the density of the liquid fuel is, the higher the mass of the fuel carried by the aircraft is; the higher the volumetric heat value of the fuel, the higher the energy released by consuming per unit volume of the fuel. These characteristics of the fuel will be more beneficial to the performances of the aircrafts in various aspects. Alternatively, on the premise of keeping the performances of aircrafts unchanged, using a high density fuel can reduce the volume of used oil tanks, minimize the volume of the aircrafts, and increase the penetration ability and mobility of the aircrafts.

Fused-ring alkane fuel is a kind of liquid fuel having high density, high heat value, low freezing point and high thermal stability. For example, decalin has a molecular density of 0.88 g/mL, a freezing point of less than $-30°$ C., and a net combustion heat value of more than 37.4 MJ/L, and it is excellent in thermal stability. Thus, this material is a main component of high density thermally stable jet fuels (e.g., JP-900). There are many reports regarding processes of preparing the fused-cycle alkane fuel molecules. In the document "Sustainable Chemistry & Engineering, 2016, 4, 6160" in the document ACS reports, by taking cyclopentanol as a raw material, the cyclopentanol is catalytically dehydrated to produce cyclopentene, then the cyclopentene takes an intermolecular alkylation reaction to produce a fuel precursor such as decalin, and at last, the fuel precursor is hydrogenated under high pressure to produce a mixture of decalin (77 wt %) and $C_{15}$ alkanes, the mixture having a density of 0.90 g/mL. In the document "Chemical Engineering Science, 2018, 180, 64", concentrated sulfuric acid is utilized to catalyze the one-pot reaction of a cyclic alcohol and a branched cycloalkane to perform continuous dehydration, alkylation, rearrangement and hydrogen transfer, thereby to obtain branched naphthalene alkanes having a density of 0.88 g/mL or above and a freezing point as low as $-110°$ C. However, these processes have complicated procedures and complex operations, or they will produce strong corrosions to associated apparatus, or they have a low selectivity to fused-ring alkane products. Thus, it is a challenge to produce fused-ring multi-ring alkane fuel with high selectivity under mild conditions.

SUMMARY

The object of the invention is to provide a high density fuel molecule of substituted fused-ring alkane that is prepared by using a photocatalytic process. The process has the advantages of mild process conditions, high substrate universality, and high selectivity to target product.

A first aspect of the invention relates to a fused-ring alkane fuel characterized in that the fuel has the following structure:

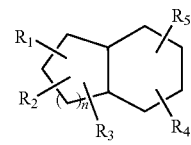

wherein n is 1 or 2; $R_1$, $R_2$, $R_3$, $R_4$ and $R_5$ are H or $-CH_3$ or $-CH_2CH_3$.

Preferably, the fuel has a density of greater than 0.870 $g/cm^3$, a freezing point of not higher than $-50°$ C., and a net mass heat value of not less than 42.0 MJ/kg.

A second aspect of the invention discloses a process for the preparation of the fused-ring alkane fuel, characterized in that the process includes the steps of:

(1) In the presence of ultraviolet light and a photocatalyst, a Diels-Alder cycloaddition reaction between a substituted or unsubstituted cycloenone and a substituted or unsubstituted furan molecule occurs to produce a fuel precursor molecule:

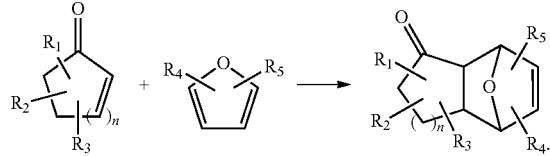

(2) Under certain conditions, the fuel precursor molecule obtained in the step (1) is subjected to hydrodeoxygenation to produce the fused-ring alkane fuel:

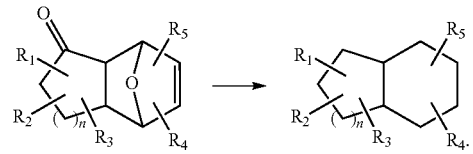

Preferably, the photocatalyst in the step (1) is one or more selected from the group of ZnO/HZSM-5, ZnO/Na-ZSM, ZnO/Hβ, ZnO/HY, ZnO/LaY, Ti-MCM-41, $TiO_2/Al_2O_3$, $TiO_2/SiO_2$, $TiO_2/MK$-10, $TiO_2/SBA$-15, P25, $ZnO/C_3N_4$, $TiO_2/C_3N_4$, $ZnO/WO_3$, $TiO_2/WO_3$, $C_3N_4$, $WO_3$, $WO_{2.72}$. The photocatalyst is added in an amount of 1 to 20% by weight of the reactants; the reaction temperature ranges from $-40°$ C. and $30°$ C., and the reaction time ranges from 9 h to 24 h.

Preferably, the substituted or unsubstituted cycloenones as described in the step(1) is one or more selected from the group of cyclopentenone, 3-methyl-2-cyclopentenone, 4-methyl-2-cyclopentenone, 5-methyl-2-cyclopentenone, 4,4'-dimethyl-2-cyclopentenone, 3,4-dimethyl-2-cyclopentenone, 3,5-dimethyl-2-cyclopentenone, 4,5-dimethyl-2-cyclopentenone, 3,4,4'-trimethyl-2-cyclopentenone, 3,4,5-trimethyl-2-cyclopentenone, 3-ethyl-2-cyclopentenone, 4-ethyl-2-cyclopentenone, 5-ethyl-2-cyclopentenone, 4,4'-diethyl-2-cyclopentenone, 3,4-diethyl-2-cyclopentenone, 3,5-diethyl-2-cyclopentenone, 4,5-diethyl-2-cyclopentenone, 3,4,4'-triethyl-2-cyclopentenone, 3,4,5-triethyl-2-cyclopentenone, cyclohexenone, 2-methyl-2-cyclohexenone, 3-methyl-2-cyclohexenone, 4-methyl-2-cyclohexenone, 5-methyl-2-cyclohexenone, 6-methyl-2-cyclohexenone, 2,3-dimethyl-2-cyclohexenone, 2,4-dimethyl-2-cyclohexenone, 2,5-dimethyl-2-cyclohexenone, 2,6-dimethyl-2-cyclohexenone, 3,4-dimethyl-2-cyclohexenone, 3,5-dimethyl-2-cyclohexenone, 3,6-dimethyl-2-cyclohexenone, 4,5-dimethyl-2-cyclohexenone, 4,6-dimethyl-2-cyclohexenone, 5,6-dimethyl-2-cyclohexenone, 2-ethyl-2-cyclohexenone, 3-ethyl-2-cyclohexenone, 4-ethyl-2-cyclohexenone, 5-ethyl-2-cyclohexenone, 6-ethyl-2-cyclohexenone, 2,3-diethyl-2-cyclohexenone, 2,4-diethyl-2-cyclohexenone, 2,5-diethyl-2-cyclohexenone, 2,6-diethyl-2-cyclohexenone, 3,4-diethyl-2-cyclohexenone, 3,5-diethyl-2-cyclohexenone, 3,6-diethyl-2-cyclohexenone, 4,5-diethyl-2-cyclohexenone, 4,6-diethyl-2-cyclohexenone, 5,6-diethyl-2-cyclohexenone, 2,3,4-trimethyl-2-cyclohexenone, 2,3,5-trimethyl-2-cyclohexenone, 2,3,6-trimethyl-2-cyclohexenone, 3,4,5-trimethyl-2-cyclohexenone, 3,4,6-trimethyl-2-cyclohexenone and 4,5,6-trimethyl-2-cyclohexenone.

The substituted or unsubstituted furan is one or more selected from the group of furan, 2-methylfuran, 3-methylfuran, 2,3-dimethylfuran, 2,4-dimethylfuran, 2,5-dimethylfuran, 2-ethylfuran, 3-ethylfuran, 2,3-diethylfuran, 2,4-diethylfuran and 2,5-diethylfuran.

The substituted or unsubstituted cycloenones is not higher than 40 wt % based on the total mass of the substituted or unsubstituted cycloenones and the substituted or unsubstituted furan.

Preferably, the fuel precursor molecule in the step (2) is hydrodeoxygenated under the following conditions: in the presence of a hydrodeoxygenation catalyst, a reaction temperature of 200° C. to 280° C., a hydrogen gas pressure of 4 MPa to 8 MPa, and a reaction time of 24 h to 48 h.

Preferably, the hydrodeoxygenation catalyst is one or more of copper, nickel, platinum, gold or palladium loaded on one or more of supporters $Al_2O_3$, $SiO_2$, HZSM-5, MCM-41, Hβ, SBA-15 or HY. The hydrodeoxygenation catalyst is added in an amount of 1 to 40% by weight of the fuel precursor molecule.

Preferably, the ultraviolet light in the step (1) is light having a wavelength between 300 nm and 360 nm.

A third aspect of the invention discloses the use of the photocatalyst in step (1) for increasing the selectivity to the target product of a cycloaddition reaction between a substituted or unsubstituted cycloenones and a substituted or unsubstituted furan molecule.

The invention has the following advantages.
1. The fused-ring alkane fuels of the invention have excellent performances of high density, high heat value, low freezing point, and high thermal stability, and particularly, the density that is far higher than that of traditional aviation kerosene (the density is generally 0.78 g/mL). For aerospace crafts with limited volume of oil tanks, the fuels can effectively increase oil carrying quality and satisfy application requirements in long flying range, high flying speed, and large load.
2. After adding a photocatalyst to the Diels-Alder cycloaddition reaction of the invention, the selectivity to the target product of the photocatalytic reaction (i.e., the [2+4] cycloaddition reaction between substituted or unsubstituted cycloenones and substituted or unsubstituted furan molecules) is greatly increased, while the photochemical [2+2] products of the substituted or unsubstituted cycloenones per se and the photochemical [2+2] products of the reaction between the substituted or unsubstituted cycloenones and the substituted or unsubstituted furansare greatly reduced (see Examples 1 and 2 of the invention). Thereby, the quality of the fused-ring alkane fuels of the invention is greatly improved.
3. The photocatalytic process for preparation of the fused-ring alkane fuels of the invention may be performed via a Diels-Alder reaction of heterogeneous system and a hydrodeoxygenation reaction at normal temperature and at normal pressure, and the process has the advantages of mild process conditions, high substrate universality and high selectivity to target products. Thus, the process has a great value in industrial application.

DETAILED DESCRIPTION OF THE EMBODIMENTS

The invention is further illustrated by combining the following examples, and the examples are only illustrative but not limited. Table 1 shows the synthesis reaction of the fuel precursor molecules in Examples 1-30.

TABLE 1

Fuel Precursor molecule Synthesis Reactions

| Serial No. | Raw materials (mass ratio) | Raw material mass/g | Catalyst | Catalyst amount (in reactant)/ wt % | Reaction temperature/° C. | Reaction time/h | Yield of fuel precursor molecules/% |
| --- | --- | --- | --- | --- | --- | --- | --- |
| Example 1 | 30% cyclopentenone 70% furan | 20 | None | 10 | 10 | 24 | 30 |
| Example 2 | 30% cyclopentenone 70% furan | 20 | ZnO/HZSM-5 | 10 | 10 | 24 | 90 |
| Example 3 | 30% of 4,4'-dimethyl-2-cyclopentenone 70% furan | 20 | ZnO/HZSM-5 | 5 | 30 | 24 | 80 |

TABLE 1-continued

Fuel Precursor molecule Synthesis Reactions

| Serial No. | Raw materials (mass ratio) | Raw material mass/g | Catalyst | Catalyst amount (in reactant)/ wt % | Reaction temperature/° C. | Reaction time/h | Yield of fuel precursor molecules/% |
|---|---|---|---|---|---|---|---|
| Example 4 | 20% of 3,4,5-trimethyl-2-cyclopentenone 80% furan | 20 | ZnO/HZSM-5 | 20 | 30 | 24 | 89 |
| Example 5 | 40% cyclohexenone 60% furan | 20 | ZnO/HY | 1 | −40 | 20 | 66 |
| Example 6 | 30% 2-methyl-2-cyclohexenone 70% furan | 20 | ZnO/HY | 10 | 10 | 24 | 83 |
| Example 7 | 20% 3,5-dimethyl-2-cyclohexenone 80% furan | 20 | ZnO/LaY | 10 | 10 | 24 | 82 |
| Example 8 | 10% 2,3,5-trimethyl-2-cyclohexenone 90% furan | 20 | ZnO/LaY | 10 | 25 | 24 | 78 |
| Example 9 | 20% of 3-ethyl-2-cyclopentenone 80% furan | 20 | Ti-MCM-41 | 10 | 30 | 24 | 86 |
| Example 10 | 30% of 3-ethyl-2-cyclohexenone 70% 2-methylfuran | 20 | Ti-MCM-41 | 20 | 0 | 24 | 88 |
| Example 11 | 30% of 3-ethyl-2-cyclohexenone 70% 2-methylfuran | 20 | Ti-MCM-41 | 10 | 0 | 24 | 82 |
| Example 12 | 20% 3-Ethyl-2-cyclohexenone 80% 2-methylfuran | 20 | Ti-MCM-41 | 20 | 0 | 24 | 90 |
| Example 13 | 30% cyclopentenone 70% 2-methylfuran | 20 | $TiO_2/SiO_2$ | 10 | 10 | 10 | 85 |
| Example 14 | 40% of 3-methyl-2-cyclopentenone 60% 2-methylfuran | 20 | $TiO_2/SiO_2$ | 10 | 10 | 9 | 80 |
| Example 15 | 30% of 4,4'-dimethyl-2-cyclopentenone 70% 2-methylfuran | 20 | $TiO_2/MK-10$ | 10 | 0 | 9 | 86 |
| Example 16 | 30% of 3,4,5-trimethyl-2-cyclopentenone 70% 2-methylfuran | 20 | $TiO_2/MK-10$ | 10 | 0 | 12 | 90 |
| Example 17 | 20% cyclohexenone 80% 2,3-dimethylfuran | 20 | ZnO/HY | 5 | 15 | 9 | 93 |
| Example 18 | 30% 3-methyl-2-cyclohexenone 70% 2,3-dimethylfuran | 20 | ZnO/HY | 5 | 15 | 9 | 89 |
| Example 19 | 30% 3,5-dimethyl-2-cyclohexenone 70% 2,4-dimethylfuran | 20 | $TiO_2/SBA-15$ | 5 | 0 | 9 | 83 |
| Example 20 | 20% 2,3,5-trimethyl-2-cyclohexenone 80% 2-ethylfuran | 20 | $TiO_2/SBA-15$ | 5 | 0 | 12 | 92 |
| Example 21 | 40% of 3-ethyl-2-cyclopentenone 60% 2,3-diethylfuran | 20 | $TiO_2/Al_2O_3$ | 5 | 20 | 9 | 84 |

TABLE 1-continued

Fuel Precursor molecule Synthesis Reactions

| Serial No. | Raw materials (mass ratio) | Raw material mass/g | Catalyst | Catalyst amount (in reactant)/ wt % | Reaction temperature/° C. | Reaction time/h | Yield of fuel precursor molecules/% |
|---|---|---|---|---|---|---|---|
| Example 22 | 10% 3-ethyl-2-cyclohexenone 90% 2,4-diethylfuran | 20 | P25 | 5 | 20 | 9 | 92 |
| Example 23 | 40% cyclohexenone 60% 2,5-diethylfuran | 20 | P25 | 10 | −40 | 24 | 82 |
| Example 24 | 40% cyclohexenone 60% 2,5-dimethylfuran | 20 | ZnO/Hbeta | 10 | −40 | 24 | 85 |
| Example 25 | 40% cyclopentenone 60% 2,5-dimethylfuran | 20 | ZnO/Hbeta | 10 | −40 | 24 | 88 |
| Example 26 | 40% cyclopentenone 60% 2,5-dimethylfuran | 20 | ZnO/Hbeta | 10 | 10 | 24 | 90 |
| Example 27 | 40% cyclopentenone 60% 2,5-dimethylfuran | 20 | ZnO/$C_3N_4$ | 10 | 10 | 24 | 91 |
| Example 28 | 40% cyclopentenone 60% 2,5-dimethylfuran | 20 | $TiO_2$/$C_3N_4$ | 10 | 10 | 24 | 85 |
| Example 29 | 40% cyclopentenone 60% 2,5-dimethylfuran | 20 | ZnO/$WO_3$ | 10 | 10 | 24 | 83 |
| Example 30 | 40% cyclopentenone 60% 2,5-dimethylfuran | 20 | $TiO_2$/$WO_3$ | 10 | 10 | 24 | 81 |

The specific reaction steps are exemplified by Example 1 in Table 1: in a 25 mL single-port jacketed glass reactor, 6 g of cyclopentenone and 14 g of furan were added and bubbled with nitrogen gas for 0.5 h whiling being stirring, and then the reactor was sealed; a circulation with 10° C. water started and the reaction mixture was irradiated by a high-pressure mercury lamp for 24 h; the obtained fuel precursor molecules were analyzed by using gas chromatography-mass spectrometry, and the result shows that the yield of the target product, [2+4] cycloaddition fuel precursor molecule A, was 30%, and the others were the by-products of the [2+2] product B of the photochemical reaction of the cyclopentenone per se and the [2+2] product C of the photochemical reaction between the cyclopentenone and the furan; the reaction was described in the following scheme:

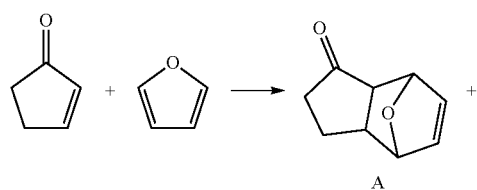

A

B

C

Example 2 was conducted by adding 2 g of a photocatalyst ZnO/HZSM-5 on the basis of Example 1, and the other reaction conditions were the same as those in Example 1. The results show that the yield of the fuel precursor molecules A was 90%. Clearly, adding the photocatalyst can significantly increase the selectivity to the target product of the Diels-Alder reaction. The reaction conditions and yields of Examples 3-30 were shown in Table 1. As seen from Table 1, the selectivity to the target product, the [2+4] cycloaddition fuel precursor molecules, of the photocatalytic Diels-Alder reaction was greatly improved.

Table 2 shows the reaction conditions and results of Examples 31 to 52 in which the fuel precursor molecules of Examples 1-30 in Table 1 were hydrodeoxygenated to produce the fused-ring alkane fuels (the fuel precursor molecules obtained in Examples 1 and 2 have the same structure; the fuel precursor molecules obtained in Examples 10, 11, and 12 have the same structure; the fuel precursor molecules obtained in Examples 25, 26, 27, 28, 29 and 30 have the same structure).

TABLE 2

Hydrodeoxygenation Reaction of Fuel Precursor Molecules

| Serial No. | Reactant (fuel precursor molecules 20 g) | Catalyst (mass) | Hydrogen pressure/MPa | Reaction temperature/° C. | Reaction time/h |
|---|---|---|---|---|---|
| Example 31 | Example 1 | 5 g Pd/HY | 6 | 200 | 24 |
| Example 32 | Example 3 | 5 g Pd/Hβ | 6 | 200 | 24 |
| Example 33 | Example 4 | 5 g Pd/HZSM-5 | 6 | 200 | 24 |
| Example 34 | Example 5 | 5 g Pt/HZSM-5 | 6 | 200 | 48 |
| Example 35 | Example 6 | 5 g Pt/HY | 6 | 200 | 48 |
| Example 36 | Example 7 | 5 g Pt/HY | 6 | 200 | 48 |
| Example 37 | Example 8 | 8 g Ni/HZSM-5 | 8 | 250 | 48 |
| Example 38 | Example 9 | 8 g Ni/HY | 8 | 250 | 48 |
| Example 39 | Example 10 | 8 g Ni/Hβ | 8 | 250 | 48 |
| Example 40 | Example 13 | 8 g Cu/HZSM-5 | 8 | 280 | 48 |
| Example 41 | Example 14 | 8 g Cu/HY | 8 | 280 | 48 |
| Example 42 | Example 15 | 8 g Cu/Hβ | 8 | 280 | 48 |
| Example 43 | Example 16 | 5 g Au/HZSM-5 | 4 | 200 | 48 |
| Example 44 | Example 17 | 5 g Au/HY | 4 | 200 | 48 |
| Example 45 | Example 18 | 5 g Au/Hβ | 4 | 200 | 24 |
| Example 46 | Example 19 | 5 g Pd/SBA-15 | 6 | 200 | 24 |
| Example 47 | Example 20 | 5 g Pt/SBA-15 | 6 | 200 | 24 |
| Example 48 | Example 21 | 5 g Au/SBA-15 | 6 | 200 | 24 |
| Example 49 | Example 22 | 8 g Ni/SiO$_2$ | 8 | 200 | 48 |
| Example 50 | Example 23 | 5 g Pd/HY | 6 | 200 | 24 |
| Example 51 | Example 24 | 5 g Pd/HZSM-5 | 6 | 200 | 24 |
| Example 52 | Example 25 | 8 g Ni/HZSM-5 | 8 | 250 | 24 |

The hydrodeoxygenation reaction of the fuel precursor molecules is exemplified by Example 35 of Table 2, and the specific steps are described as follows: a 100 mL autoclave were charged with 20 g of the fuel precursor molecules obtained in Example 6 and 5 g of a catalyst Pd/HZSM-5, sealed, replaced with N$_2$ for three times, and then charged with 6 MPa of H$_2$, and the mixture was raised to temperature 200° C. with stirring and reacted for 24 h; the reaction solution was analyzed by using gas chromatography-mass spectrometry, to qualitatively determine the product and calculate the reaction yield; the fuel precursor molecules were fully converted, and the target product of fused ring alkaline fuel molecules has the yield of 91%; the reaction conditions and product yields of the other examples are shown in Table 2.

The fused-ring alkane fuel obtained in Example 35 was measured to have a density of 0.896 g/cm$^3$, a freezing point of less than −70° C., and a mass heat value of 42.4 MJ/kg. The measurement results of the fused-ring alkane fuels obtained in the other examples are shown in Table 3.

TABLE 3

Properties of Fused-ring alkane Fuels Obtained in Examples 31-52

| Serial No. | Density (g/cm$^3$) | Freezing point (° C.) | Mass heat value (MJ/kg) |
|---|---|---|---|
| Example 31 | 0.883 | −52 | 42.1 |
| Example 32 | 0.879 | −60 | 42.3 |
| Example 33 | 0.875 | −60 | 42.5 |
| Example 34 | 0.906 | −57 | 42.3 |
| Example 35 | 0.896 | <−70 | 42.4 |
| Example 36 | 0.892 | <−70 | 42.5 |
| Example 37 | 0.890 | <−70 | 42.7 |
| Example 38 | 0.887 | <−70 | 42.8 |
| Example 39 | 0.886 | <−70 | 43.1 |
| Example 40 | 0.880 | −63 | 42.3 |
| Example 41 | 0.876 | −70 | 42.4 |
| Example 42 | 0.876 | −68 | 42.4 |
| Example 43 | 0.872 | <−70 | 43.2 |
| Example 44 | 0.884 | −68 | 42.5 |
| Example 45 | 0.880 | <−70 | 42.9 |
| Example 46 | 0.881 | <−70 | 43.0 |
| Example 47 | 0.876 | <−70 | 42.9 |
| Example 48 | 0.874 | <−70 | 43.4 |
| Example 49 | 0.872 | <−70 | 43.5 |
| Example 50 | 0.872 | <−70 | 43.1 |

TABLE 3-continued

Properties of Fused-ring alkane Fuels Obtained in Examples 31-52

| Serial No. | Density (g/cm³) | Freezing point (° C.) | Mass heat value (MJ/kg) |
|---|---|---|---|
| Example 51 | 0.885 | −60 | 42.4 |
| Example 52 | 0.875 | <−70 | 42.5 |

From the above results, it can be seen that a substituted or unsubstituted furan and a substituted or unsubstituted cycloenones may prepare the fused-ring alkane fuels in a high selectivity and a high yield through a heterogeneous photocatalytic Diels-Alder cycloaddition reaction and then through a hydrodeoxygenation reaction. The resultant fused-ring alkane fuels have excellent performances of high density, high heat value, low freezing point, and high thermal stability.

What is claimed is:

1. A process for preparing a fused-ring alkane fuel, wherein the fused-ring alkane fuel has the following structure:

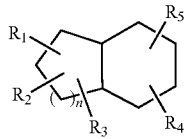

wherein n is 1 or 2; $R_1$, $R_2$, $R_3$, $R_4$ and $R_5$ are H or —$CH_3$ or —$CH_2CH_3$;

the fused-ring alkane fuel has a density of greater than 0.870 g/cm³, a freezing point of not higher than −50° C., and a net mass heat value of not less than 42.0 MJ/kg; and the process for preparing a fused-ring alkane fuel, wherein the process comprises steps of:

(1) in a presence of ultraviolet light and a photocatalyst, a Diels-Alder cycloaddition reaction between a substituted or unsubstituted cyclic enone and a substituted or unsubstituted furan molecule occurs to produce a fuel precursor molecule:

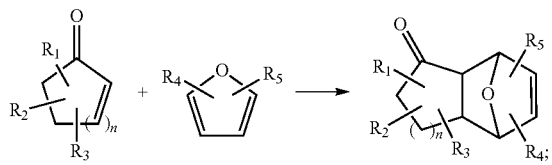

(2) the fuel precursor molecule obtained in the step (1) is subjected to hydrodeoxygenation to produce the fused-ring alkane fuel.

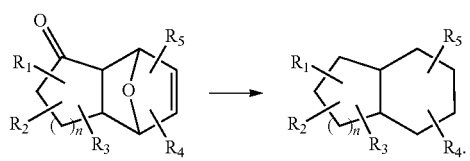

2. The process according to claim 1, wherein the photocatalyst in the step (1) is one or more selected from the group consisting of ZnO/HZSM-5, ZnO/Na-ZSM, ZnO/Hβ, ZnO/HY, ZnO/LaY, Ti-MCM-41, $TiO_2$/$Al_2O_3$, $TiO_2$/$SiO_2$, $TiO_2$/MK-10, $TiO_2$/SBA-15, P25, ZnO/$C_3N_4$, $TiO_2$/$C_3N_4$, ZnO/$WO_3$, $TiO_2$/$WO_3$, $C_3N_4$, $WO_3$, and $WO_{2.72}$, wherein the photocatalyst is added in an amount of 1% to 20% by weight of reactants; a reaction temperature ranges from −40° C. and 30° C., and a reaction time ranges from 9 h to 24 h.

3. The process according to claim 1, wherein the substituted or unsubstituted cyclic enone in the step (1) is one or more selected from the group consisting of cyclopentenone, 3-methyl-2-cyclopentenone, 4-methyl-2-cyclopentenone, 5-methyl-2-cyclopentenone, 4,4'-dimethyl-2-cyclopentenone, 3,4-dimethyl-2-cyclopentenone, 3,5-dimethyl-2-cyclopentenone, 4,5-dimethyl-2-cyclopentenone, 3,4,4'-trimethyl-2-cyclopentenone, 3,4,5-trimethyl-2-cyclopentenone, 3 -ethyl-2-cyclopentenone, 4-ethyl-2-cyclopentenone, 5-ethyl-2-cyclopentenone, 4,4'-diethyl-2-cyclopentenone, 3,4-diethyl-2-cyclopentenone, 3,5-diethyl-2-cyclopentenone, 4,5-diethyl-2-cyclopentenone, 3,4,4'-triethyl-2-cyclopentenone, 3,4,5-triethyl-2-cyclopentenone, cyclohexenone, 2-methyl-2-cyclohexenone, 3-methyl-2-cyclohexenone, 4-methyl-2-cyclohexenone, 5-methyl-2-cyclohexenone, 6-methyl-2-cyclohexenone, 2,3-dimethyl-2-cyclohexenone, 2,4-dimethyl-2-cyclohexenone, 2,5-dimethyl-2-cyclohexenone, 2,6-dimethyl-2-cyclohexenone, 3,4-dimethyl-2-cyclohexenone, 3,5-dimethyl-2-cyclohexenone, 3,6-dimethyl-2-cyclohexenone, 4,5-dimethyl-2-cyclohexenone, 4,6-dimethyl-2-cyclohexenone, 5,6-dimethyl-2-cyclohexenone, 2-ethyl-2-cyclohexenone, 3-ethyl-2-cyclohexenone, 4-ethyl-2-cyclohexenone, 5-ethyl-2-cyclohexenone, 6-ethyl-2-cyclohexenone, 2,3-diethyl-2-cyclohexenone, 2,4-diethyl-2-cyclohexenone, 2,5-diethyl-2-cyclohexenone, 2,6-diethyl-2-cyclohexenone, 3,4-diethyl-2-cyclohexenone, 3,5-diethyl-2-cyclohexenone, 3,6-diethyl-2-cyclohexenone, 4,5-diethyl-2-cyclohexenone, 4,6-diethyl-2-cyclohexenone, 5,6-diethyl-2-cyclohexenone, 2,3,4-trimethyl-2-cyclohexenone, 2,3,5-trimethyl-2-cyclohexenone, 2,3,6-trimethyl-2-cyclohexenone, 3,4,5-trimethyl-2-cyclohexenone, 3,4,6-trimethyl-2-cyclohexenone, 4,5,6-trimethyl-2-cyclohexenone, and 4,5,6-trimethyl-2-cyclohexenone;

the substituted or unsubstituted furan is one or more selected from the group consisting of furan, 2-methylfuran, 3-methylfuran, 2,3-dimethylfuran, 2,4-dimethylfuran, 2,5-dimethylfuran, 2-ethylfuran, 3-ethylfuran, 2,3-diethylfuran, 2,4-diethylfuran and 2,5-diethylfuran;

wherein the substituted or unsubstituted cyclic enone is not higher than 40 wt % based on a total mass of the substituted or unsubstituted cyclic enone and the substituted or unsubstituted furan.

4. The process according to claim 1, wherein the fuel precursor molecule in the step (2) is hydrodeoxygenated under the following conditions: in a presence of a hydrodeoxygenation catalyst, a reaction temperature of 200° C. to 280° C., a hydrogen gas pressure of 4 MPa to 8 MPa, and a reaction time of 24 h to 48 h.

5. The process according to claim 4, wherein the hydrodeoxygenation catalyst is one or more of copper, nickel, platinum, gold or palladium loaded on one or more of supporters $Al_2O_3$, $SiO_2$, HZSM-5, MCM-41, Hβ, SBA-15 or HY; the hydrodeoxygenation catalyst is added in an amount of 1% to 40% by weight of the fuel precursor molecule.

6. The process according to claim 1, wherein the ultraviolet light in the step (1) is a light having a wavelength between 300 nm and 360 nm.

7. The process according to claim 1, wherein the photocatalyst in the step (1) increases a selectivity to a target product of the Diels-Alder cycloaddition reaction between the substituted or unsubstituted cyclic enone and the substituted or unsubstituted furan molecule.

8. The process according to claim 2, wherein the ultraviolet light in the step (1) is a light having a wavelength between 300 nm and 360 nm.

9. The process according to claim 2, wherein the photocatalyst in the step (1) increases a selectivity to a target product of the Diels-Alder cycloaddition reaction between the substituted or unsubstituted cyclic enone and the substituted or unsubstituted furan molecule.

* * * * *